United States Patent [19]

Stautzenberger et al.

[11] Patent Number: 4,803,295

[45] Date of Patent: Feb. 7, 1989

[54] PURIFICATION OF DIPHENYL PHTHALATES

[75] Inventors: A. Lee Stautzenberger; Robert W. Kunkel, both of Nueces, Tex.

[73] Assignee: Hoechst Celanese Corporation, Bridgewater, N.J.

[21] Appl. No.: 100,493

[22] Filed: Sep. 24, 1987

[51] Int. Cl.$^4$ .............................................. C07C 67/48
[52] U.S. Cl. ......................................... 560/78; 560/86
[58] Field of Search ..................................... 560/78, 86

[56] References Cited

U.S. PATENT DOCUMENTS

| | | | |
|---|---|---|---|
| 2,043,688 | 6/1936 | Woodhouse | 560/78 |
| 2,780,643 | 2/1957 | Buchner | 560/78 X |
| 3,487,100 | 12/1969 | Arai et al. | 560/79 |
| 4,076,946 | 2/1978 | Millick | 560/78 |

Primary Examiner—Werren B. Lone
Assistant Examiner—Vera C. Clarke
Attorney, Agent, or Firm—Depaoli & O'Brien

[57] ABSTRACT

Color properties of crude phenolic esters of aromatic dicarboxylic acids are improved by subjecting the esters to hydrogenation in the presence of hydrogen and a hydrogenation catalyst.

5 Claims, No Drawings

PURIFICATION OF DIPHENYL PHTHALATES

BACKGROUND OF THE INVENTION

1. Field of the Invention

The present invention relates to the purification of phenolic esters of aromatic carboxylic acids and more particularly to the purification of diphenyl esters of aromatic carboxylic acids, such as phthalic acids, to provide ester monomers having good color properties.

2. Description of the Prior Art

The production of various phenolic esters of aromatic benzenedicarboxylic acids, such as diphenyl terephthalate, have become of significant commercial interest in recent years due to their use in a great many types of processes. As an example, diphenyl terephthalate and diphenyl isophthalate when dissolved in a solvent may be reacted with a primary diamine to produce polyamides. Likewise, 3,3'-diaminobenzidine may be condensed with various diphenyl esters to form polybenzimidazoles. In the synthesis of polyarylate engineering resins, such as Durel ®, a mixture of iso- and terephthalates is reacted with bisphenol A to provide resins which are of significant commercial interest. These esters may be produced by reaction of acid chlorides with a phenol to produce the phenyl ester and hydrogen chloride as a by-product, or by reacting a phenolic compound and aromatic dicarboxylic acid in the presence of a catalyst consisting of an alkali metal compound and a boron compound. While such processes are effective for producing phenolic esters they suffer the disadvantage that during the process of esterification, the ester acquires a pink to dark brown color which present methods of purification, such as vacuum distillation, recrystallization and/or carbon treatment, are insufficient to remove. Accordingly, there is a need for additional purification methods which are sufficient to achieve specification grade diphenyl phthalates.

U.S. Pat. No. 2,780,643 discloses subjecting synthetic alcohols to hydrogenation for color improvement followed by esterification of the alcohol with phthalic acid. U.S. Pat. No. 3,487,100 discloses purification of crude bis-B-hydroxyethyl terephthalate (BHET) for color improvement by reducing an aqueous solution of BHET in the presence of hydrogen and a hydrogenation catalyst. U.S. Pat. No. 4,076,946 discloses a process in which molten dimethyl terephthalate containing aldehydic impurities is subject to catalytic hydrogenation, without significant ring hydrogenation, to reduce the aldehydic impurities to compounds which can be tolerated in fiber grade polyethylene terephthalate.

SUMMARY OF THE INVENTION

The present invention is directed to an improvement in the purification of phenolic esters of aromatic carboxylic acids, especially the diphenyl esters, by subjecting such ester to hydrogenation with hydrogen in the presence of a hydrogenation catalyst.

DESCRIPTION OF THE INVENTION

In carrying out the invention crude diphenyl esters, such as diphenyl isophthalate, are dissolved in a suitable inert organic solvent, preferably a hydrocarbon or chlorinated hydrocarbon solvent such as benzene, toluene, or methylene chloride. The amount of solvent is not critical and the amount thereof should be sufficient to completely dissolve the phenolic ester. Mixtures of two or more solvents also can be employed in the method of the invention.

The crude phenolic ester and solvent are charged to a reactor, preferably a stirred autoclave, which contains a hydrogenation catalyst and the hydrogenation is carried out at temperatures of 30° C. to 175° C., preferably about 80° C. to 160° C., in the presence of molecular hydrogen. Hydrogen is introduced into the autoclave to establish a hydrogen pressure ranging from about 100 to 1200 psig, and preferably about 200–800 psig. The residence time for the hydrogenation of crude diphenyl esters under the aforesaid temperature and pressure is for a period of time, usually less than about eight hours, sufficient to result in a substantial reduction in the color properties of the esters without significant hydrogenation of the aromatic ring structure or deleterious hydrogenolysis. As shown hereinafter, good color properties of crude diphenyl phthalate esters are achieved in a batch operation at temperature of 100° C. with a residence time of one hour. At the completion of the hydrogenation reaction the catalyst is removed by filtration and the hot filtrate is cooled to crystallize diphenyl phthalate, which is then vacuum dried in an oven. Cooling is preferably within a temperature range of 25° C. to about 60° C., or the filtered solution may be evaporated to remove most of the solvent. The process also may be carried out continuously by maintaining the crude diphenyl ester in the reactor for a suitable residence time. The color and purity can further be improved by a flash, vacuum distillation at 1–2 torr, which will separate any inorganics (catalyst from the ester synthesis, etc.) and some color bodies not removed by hydrogenation.

The hydrogenation catalyst used for purposes of the invention can be any known hydrogenation catalyst. Representative of such catalysts are platinum, palladium, rhodium, ruthenium, nickel, cobalt, etc., which may be unsupported or supported with a carrier material such as acidic clay or amorphous silica-alumina. Zeolites such as zeolites X and Y are also useful support materials. Raney nickel or cobalt are especially preferred catalysts, which give a minimum of ring hydrogenation.

The amount of catalyst used is preferably within the range of 0.01 to 10 weight percent, preferably 0.5 to 5.0 weight percent, based on the weight of the ester.

The esters are derived from aromatic carboxylic acids which should be essentially free of aldehydic and ketonic carbonyl groups as these groups interfere with the esterification reaction. Other than these aldo and keto groups, the aromatic carboxylic acid may contain various functional groups which will not interfere with the esterification reaction. Generally the aromatic carboxylic acid will contain no functional groups or radicals other than carboxyl, carboxylic ester, ether, thioether, aromatic ring-substituted halo, sulfo, and sulfonyl. The aromatic carboxylic acids which are free of ketonic and aldehydic carbonyl groups have the formula:

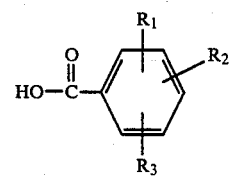

wherein $R_1$ and $R_2$ are alike or different and correspond to hydrogen, carboxyl or hydroxyl and wherein $R_3$ is hydrogen or an organic radical of six to 20 carbon atoms containing an aromatic ring, which organic radical is composed only of elements selected from the groups consisting of carbon, hydrogen, and oxygen.

Especially preferred are those dicarboxylic acids of the formula

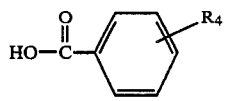

where $R_4$ is carboxyl group or a radical of seven to 20 carbon atoms of the formula

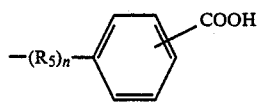

wherein n is 0 or 1 and $R_5$ is a divalent hydrocarbon radical, oxygen, or a divalent radical composed of carbon, hydrogen, and oxygen wherein the oxygen present is as an ether linkage. Among the acids containing aromatic ring-substituted carboxyl groups that may be esterified in accordance with the present invention are benzoic acid, phthalic acid, terephthalic acid, isophthalic acid, diphenic acid, homophthalic acid, toluic acid, alpha-naphthoic acid, chlorobenzoic acid, salicylic acid, 1,2-(ethylenedioxy)dibenzoic acid, and 2,5-dimethylterephthalic acid. Mixtures (3/1) of iso- and terephthalic acid are especially preferred.

The phenols utilized for production of the ester are mono functional phenols which contain only one phenolic hydroxyl group. Generally these phenols will be those of six to 15 carbon atoms of the formula

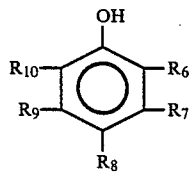

wherein $R_6$, $R_7$, $R_8$, $R_9$ and $R_{10}$ may be hydrogen, alkyl, alkaryl, aryl, or aralkyl radicals. Among the particular phenols that may be utilized are phenol, o-cresol, m-cresol, p-cresol, xylenols, either mixed or the pure isomer, o-phenylphenol, and p-phenylphenol. Of the various phenols that may be utilized, phenol itself is preferred over the others.

The esterification of a phenol with a dicarboxylic acid may be carried out at temperatures ranging from 220° C. to 290° C. in the presence of 0.01 to 3.0 mole % of organotitanate, organozirconate or organostannate catalyst, based on the amount of acid employed.

The following examples illustrate the best mode now contemplated for carrying out the invention.

EXAMPLE 1

Sixty grams of a crude diphenyl phthalate (prepared by reaction of isophthalic acid, terephthalic acid, and phenol using a zirconium tetra-n-propoxide catalyst) was dissolved in 160 ml of toluene and 4 grams of activated Raney nickel slurry (RaNi slurry in toluene, dewatered) added thereto. The mixture was then charged to a 300 ml stirred autoclave and pressured to 800 psig with hydrogen for 1 hour at 100° C. The catalyst was removed by filtration and the hot filtrate was cooled to crystallize the diphenyl phthalates which were dried in a vacuum oven. The dried material had a melt color APHA of 175 whereas a blank run without hydrogenation (essentially a recrystallization) gave a diphenyl phthalate having a melt color of 300 APHA.

EXAMPLE 2

Fifteen grams of a crude diphenyl phthalate prepared by reaction of phenol with a 3/1 mixture of isophthalic and terephthalic acid in the presence of Tyzor TE catalyst (triethanolamine titanate chelate) was dissolved in 150 ml of methylene chloride. The mixture was agitated in the presence of 1 wt.% platinum catalyst (5 wt.% mixture of platinum on active carbon) under a hydrogen pressure of about 700 psig for one hour at a temperature of 100° C. The hydrogenation catalyst was removed by filtration and the filtrate was evaporated until the solvent was gone. The remaining diphenyl phthalate was white and had an APHA color of 100.

What is claimed:

1. A method for purifying a crude diphenyl phthalate ester which comprises subjecting said ester to hydrogenation in the presence of a hydrogenation catalyst and hydrogen at temperatures ranging from about 30° C. to 175° C. for a period of time sufficient to reduce color impurities thereof, and thereafter recovering a diphenyl phthalate ester having improved color properties.

2. The method of claim 1 wherein the hydrogenation catalyst is Raney nickel.

3. The method of claim 2 wherein the temperature ranges from about 80° C. to 160° C.

4. The method of claim 3 wherein said diphenyl phthalate is prepared from the reaction of phenol with a 3/1 mixture of iso- and terephthalic acids.

5. The method of claim 4 wherein said ester is catalytically prepared in the presence of an organotitanate, organozirconate or organostannate catalyst.

* * * * *